US010377705B2

(12) United States Patent
Ho et al.

(10) Patent No.: US 10,377,705 B2
(45) Date of Patent: Aug. 13, 2019

(54) METHOD FOR PREPARING POLYARYLENE SULFIDE (PAS) MONOMER

(71) Applicant: INDUSTRIAL TECHNOLOGY RESEARCH INSTITUTE, Hsinchu (TW)

(72) Inventors: Po-Hsien Ho, Taipei (TW); Chih-Hsiang Lin, Taipei (TW); Meng-Hsin Chen, Xinpi Township (TW); Cheng-Hsing Fan, Tainan (TW); Hsin-Ching Kao, Hsinchu (TW); Yih-Her Chang, Baoshan Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/388,215

(22) Filed: Dec. 22, 2016

(65) Prior Publication Data
US 2017/0197913 A1  Jul. 13, 2017

Related U.S. Application Data

(60) Provisional application No. 62/277,091, filed on Jan. 11, 2016.

(51) Int. Cl.
C07C 321/16 (2006.01)
C07C 319/14 (2006.01)
C07C 381/12 (2006.01)
C08G 75/0204 (2016.01)
C08G 75/025 (2016.01)

(52) U.S. Cl.
CPC .......... *C07C 319/14* (2013.01); *C07C 381/12* (2013.01); *C08G 75/0204* (2013.01); *C08G 75/025* (2013.01)

(58) Field of Classification Search
CPC .. C07C 319/20; C07C 381/12; C08G 75/0204
See application file for complete search history.

(56) References Cited

U.S. PATENT DOCUMENTS

| | | | |
|---|---|---|---|
| 2,739,991 | A | 3/1956 | Hervert |
| 2,843,643 | A | 7/1958 | Gleim |
| 3,354,129 | A | 11/1967 | Edmonds, Jr. et al. |
| 3,642,772 | A | 2/1972 | Haid et al. |
| 3,775,485 | A | 11/1973 | Pilgram et al. |
| 3,987,016 | A | 10/1976 | Haddad et al. |
| 4,124,646 | A | 11/1978 | Kawamura et al. |
| 4,786,713 | A | 11/1988 | Rule et al. |
| 5,618,981 | A | 4/1997 | Shaw |
| 6,111,143 | A | 8/2000 | Park et al. |
| 8,445,629 | B2 | 5/2013 | Hinokimori et al. |
| 8,492,502 | B2 | 7/2013 | Lee et al. |

(Continued)

FOREIGN PATENT DOCUMENTS

| | | |
|---|---|---|
| CN | 1243122 A | 2/2000 |
| CN | 1209349 C | 7/2005 |

(Continued)

OTHER PUBLICATIONS

Tsuchida et al. ("Synthesis of Poly(phenylene sulfide) by O2 Oxidative Polymerization of Methyl Phenyl Sulfide", Macromolecules, vol. 27, Issue 4, Feb. 1994, pp. 1057-1060).*

(Continued)

*Primary Examiner* — Rosalynd A Keys
(74) *Attorney, Agent, or Firm* — Birch, Stewart, Kolasch & Birch, LLP

(57) ABSTRACT

A method for preparing a cationic sulfoxide intermediate having the following formula

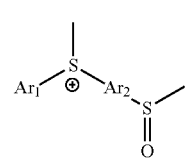

(1)

wherein $Ar_1$ and $Ar_2$ are substituted or unsubstituted aryl groups that are the same or different, includes reacting hydrogen peroxide with (i) a compound having the following formula (2) or sulfonic acid $R'SO_3H$, wherein $R'$ is $CH_3$, $CF_3$, phenyl, toluene, or OH, and (ii) a cationic thioether intermediate having the following formula (4) to obtain the cationic sulfoxide intermediate:

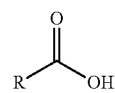

(2)

wherein R is a substituted or unsubstituted $C_1$-$C_6$ alkyl group; and

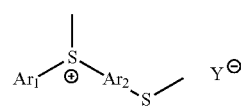

(4)

wherein $Ar_1$ and $Ar_2$ are as defined above and Y is an anion.

12 Claims, 8 Drawing Sheets

(56) References Cited

U.S. PATENT DOCUMENTS

| | | | |
|---|---|---|---|
| 8,759,478 | B2 | 6/2014 | Shin et al. |
| 8,957,182 | B2 | 2/2015 | Lee et al. |
| 9,657,141 | B2* | 5/2017 | Watanabe ............ C08G 75/029 |
| 2004/0013926 | A1 | 1/2004 | Akita et al. |
| 2005/0259398 | A1 | 11/2005 | Liu et al. |
| 2006/0200874 | A1 | 9/2006 | Castle et al. |
| 2008/0081899 | A1* | 4/2008 | Muraoka ................... C08J 7/12 |
| | | | 528/373 |
| 2014/0128568 | A1 | 5/2014 | Hinokimori |
| 2016/0200874 | A1 | 7/2016 | Watanabe et al. |

FOREIGN PATENT DOCUMENTS

| | | | |
|---|---|---|---|
| CN | 1989177 A | 6/2007 | |
| CN | 101578321 A | 11/2009 | |
| CN | 100567371 C | 12/2009 | |
| EP | 3034542 A1 | 6/2016 | |
| EP | 3042924 A1 | 7/2016 | |
| JP | 50-29511 A | 3/1975 | |
| JP | 1-78993 U | 5/1989 | |
| JP | 5-178993 A | 7/1993 | |
| JP | H5-239213 A | 9/1993 | |
| JP | 7-278099 A | 10/1995 | |
| JP | 9-48854 A | 2/1997 | |
| JP | 10-182823 A | 7/1998 | |
| JP | 10-182825 A | 7/1998 | |
| JP | 2988827 B2 | 12/1999 | |
| JP | 2992517 B1 | 12/1999 | |
| JP | 2005-330185 A | 12/2005 | |
| JP | 7-304872 A | 11/2009 | |
| JP | 2010-59159 A | 3/2010 | |
| JP | 2013-523756 A | 6/2013 | |
| JP | 2015-48447 A | 3/2015 | |
| JP | 2015-048448 | 3/2015 | |
| KR | 10-2007-0036776 A | 4/2007 | |
| KR | 20070036776 A * | 4/2007 | ............ C08G 61/12 |
| TW | 167606 | 9/1991 | |
| TW | I242567 B | 11/2005 | |
| TW | I421281 B | 1/2014 | |
| TW | 201512249 A | 4/2015 | |
| TW | 201512306 A | 4/2015 | |
| WO | WO 95/23148 A1 | 8/1995 | |
| WO | WO 2015-033936 A1 | 3/2015 | |
| WO | WO 2015-033938 A1 | 3/2015 | |

OTHER PUBLICATIONS

Schultz et al. ("New Catalysts for the Oxidation of Sulfides to Sulfones with Hydrogen Peroxide", The Journal of Organic Chemis.*
Sato et al. ("Oxidation of sulfides to sulfoxides and sulfones with 30% hydrogen peroxide under organic solvent- and halogen-free conditions", Tetrahedron 57, 2001, pp. 2469-2476).*
Haryono, A., et al, "Synthesis and Nucleophilic Dealkylation of Poly[alkyl-(4-(phenylthio)phenyl)sulfonium trifluoromethanesulfonate]s," Macromolecules, 1998, vol. 31, pp. 1202-1207.
Ho, et al., U.S. Appl. No. 15/381,684, filed Dec. 16, 2016.
Ho, et al., U.S. Appl. No. 15/389,711, filed Dec. 23, 2016.
Ho, et al., U.S. Appl. No. 15/389,785, filed Dec. 23, 2016.
Ho, et al., U.S. Appl. No. 15/393,913, filed Dec. 29, 2016.
Miyatake, K., et al, "Polymerization of Methyl Phenyl Sulfoxide under Acidic Conditions: Synthesis and X-ray Structure Analysis of a Phenylene Sulfonium Polymer," Macromolecules. 2001, vol. 34, pp. 1172-1179.
Miyatake, K., et al, "Synthesis and Proton Conductivity of Highly Sulfonated Poly(thlophenylene)," Macromolecules, 1997, vol. 30, pp. 2941-2946.
Tsuchida, E., et al, "First Phenylene Polymers Linked by Sulfonium Groups," Angew. Chem. Int. Engl., 1996, vol. 35, No. 23/24, pp. 2843-2845.
Yamamoto, K., et al, "Sulfide Bond Formation for the Synthesis of Poly(thioarylene) through Oxidation of Sulfur Chloride with Aromatics," Macromolecules, 1994, vol. 27, pp. 4312-4317.

European Notice of Allowance: issued in European Application No. 17150823.7 dated Sep. 25, 2017.
Extended European Search Report issued in European Application No. 17150788.2 dated Apr. 21, 2017.
Extended European Search Report issued in European Application No. 17150823.7 dated Apr. 18, 2017.
Extended European Search Report issued in European Application No. 17150883.1 dated Apr. 10, 2017.
Extended European Search Report issued in European Application No. 17150910.2 dated Mar. 28, 2017.
Extended European Search Report issued in European Application No. 17150978.9 dated Mar. 28, 2017.
Gabler et al., "Neue Polyphenylensulfone Reaktionen an Festen Polymeren," Chimia International Journal for Chemistry, vol. 28, No. 9, Sep. 1974, pp. 567-575, with an English abstract.
Hartke et al., "Reaction of Thioanisol with Antimony Pentachloride," Arch. Pharm., vol. 315, No. 2, 1982, pp. 153-156, with an English abstract.
Jílek et al., "Potential Metabolites of the Neuroleptic Agents Belonging to the 8-Methylthio-10-Piperazino-10, 11-Dihydrodibenzo[b,f]Thiepin Series; Synthesis of 2-Hydroxy and 3-Hydroxy Derivatives," Collection Czechoslovak Chem. Commun., Sep. 3-9, 2005, vol. 50, No. 10, Jan. 1985, pp. 2179-2190.
Ogawa et al., "Development of New Synthetic Procedure of Poly(phenylene sulfide)," Abstracts of the 37th Symposium on Main Group Element Chemistry, vol. 37, 2010, pp. 301-302, with an English abstract.
Taiwanese Notice of Allowance and Search Report issued in Taiwanese Application No. 105143834 dated Sep. 6, 2017.
Taiwanese Notice of Allowance issued in Taiwanese Application No. 105143831 dated Oct. 3, 2017.
Taiwanese Office Action and Search Report issued in Taiwanese Application No. 105142423 dated Apr. 13, 2017.
Taiwanese Office Action and Search Report issued in Taiwanese Application No. 105142916 dated Jun. 12, 2017.
Taiwanese Office Action and Search Report issued in Taiwanese Application No. 105143831 dated Jul. 3, 2017.
Tsuchida et al., "Photochemical recycling of polyarylene sulfide," Chemical Communications, No. 17, Sep. 7, 1996, pp. 2091-2092.
Tsuchida et al., "Synthesis of high molecular weight poly(phenylene sulfide) by oxidative polymerization via poly(sulfonium cation) from methyl phenyl sulfoxide," Macromolecules, vol. 26, No. 26, Dec. 20, 1993 (abstract published Nov. 15, 1993), pp. 7144-7148.
U.S. Office Action issued in U.S. Appl. No. 15/389,785 dated Sep. 29, 2017.
Ukai et al., "The reaction of phenol derivatives with sulfoxides. IV (including the reaction of sulfides and hydrogen peroxide). The synthesis of 4-thio-substituted-1,2-naphthoquinone derivatives," Chemical and Pharmaceutical Bulletin, vol. 16, No. 4, Jan. 1, 1968, pp. 606-612 (8 pages total), with an English abstract.
Yamamoto et al., "Aryl sulfide bond formation using the suifoxide-acid system for synthesis of PPS via poly(sulfonium cation) as a precursor," Journal of The American Chemical Society, vol. 115, No. 13, Jun. 1993, pp. 5819-5820.
Yamamoto et al., "Oxidative Coupling of Methyl Phenyl Sulfide via Sulfonium Formation Using an Oxovenadium Complex," The Journal of Organic Chemistry, vol. 61, No. 6, Mar. 22, 1996, pp. 1912-1913.
Yamamoto et al., "Synthesis of poly(sulfonium cation) by oxidative polymerization of aryl alkyl sulfides," The Journal of Organic Chemistry, vol. 60, No. 2, 1995, pp. 452-453.
Japanese Notice of Allowance for Application No. 2017-001902, dated Mar. 6, 2018.
Japanese Notice of Allowance for Application No. 2017-002101, dated Mar. 6, 2018.
Japanese Notification of Reasons for Rejection and English translation for Application No. 2017-001902, dated Nov. 7, 2017.
Japanese Notification of Reasons for Rejection and English translation for Application No. 2017-002101, dated Nov. 14, 2017.
Japanese Notification of Reasons for Rejection and English translation for Application No. 2017-002111, dated Feb. 27, 2018.
Taiwanese Notice of Allowance for Application No. 105142207, dated Feb. 26, 2018.

(56) References Cited

OTHER PUBLICATIONS

Taiwanese Office Action and Search Report forApplication No. 105142207, dated Dec. 19, 2017.
Taiwanese Office Action for Application No. 105142916, dated Sep. 25, 2017.
U.S. Office Action for U.S. Appl. No. 15/388,215, dated Jan. 24, 2018.
U.S. Office Action for U.S. Appl. No. 15/389,711, dated Mar. 20, 2018.
U.S. Office Action for U.S. Appl. No. 15/389,785, dated Sep. 29, 2017.
U.S. Office Action for U.S. Appl. No. 15/393,913, dated Dec. 8, 2017.
Notification of Reason(s) for Refusal issued in corresponding Japanese Application No. 2017-002112 dated Mar. 1, 2018, with English translation.
Notification of Reason(s) for Refusal issued in corresponding Japanese Application No. 2017-002113 dated Mar. 5, 2018, with English translation.
Office Action issued in corresponding European Application No. 17 150 788.2 dated Mar. 21, 2018.
Office Action issued in corresponding European Application No. 17 150 883.1 dated Mar. 21, 2018.
Office Action issued in corresponding European Application No. 17 150 910.2 dated Mar. 21, 2018.
Office Action issued in corresponding European Application No. 17 150 978.9 dated Mar. 21, 2018.
Chinese Office Action issued in corresponding Chinese Application No. 201710017862.9, and dated May 28, 2018.
Tawainese Office Action issued in corresponding Tawainese Application No. 10720446160, and dated May 17, 2018.
Chinese Office Action issued in corresponding Chinese Application No. 201710013837.3, and dated Apr. 16, 2018.
Ding et al., "Preparation of Poly(thioarylene)s from Cyclic Disulfide Oligomers," Macromolecules, vol. 30, No. 9, May 5, 1997 (Abstract published in Advance ACS Abstracts Apr. 1, 1997), 5 pages.
Japanese Notification of Reason(s) for Refusal for Japanese Application No. 2017-002111, dated Jun. 12, 2018, with English translation.
Japanese Notification of Reason(s) for Refusal for Japanese Application No. 2017-002112, dated Jul. 3, 2018, with English translation.
U.S. Office Action for U.S. Appl. No. 15/393,913, dated Aug. 15, 2018.
Decision to Grant Patent dated Nov. 27, 2018, in Japanese Patent Application No. 2017-002112.
Decision to Grant Patent dated Sep. 25, 2018, in Japanese Patent Application No. 2017-002113.
Non-Final Office Action dated Sep. 28, 2018, in U.S. Appl. No. 15/389,785.
Notice of Allowance dated Nov. 14, 2018, in Taiwan Patent Application No. 105142916.
Notice of Allowance dated Nov. 14, 2018, in Taiwan Patent Application No. 106127927.
Office Action dated Oct. 22, 2018, in Chinese Patent Application No. 201710018224.9.
Julia et al., "O-Alkylation D'Amides A L'Aide De Sels D'Alkyldiphenylsulfonium", Tetrahedron, Dec. 31, 1983, vol. 39, period 3, pp. 433-442.
Liang et al., "Advanced organic chemistry, Structure, Reaction, Synthesis", Higher Education Press, Nov. 30, 1993, p. 343.
Nenajdenko et al., "Activation of Sulfoxides with Triflic Anhydride. Synthesis of Aryldialkylsulfonium Salts and Sulfur Heterocycles", Sulfur Letters, 1996, 20(2), pp. 75-84.
Office Action issued in corresponding Chinese Application No. 201710013836.9 dated Sep. 18, 2018.
Office Action issued in corresponding Chinese Application No. 201710013837.3 dated Jan. 3, 2019.
Office Action issued in corresponding Chinese Application No. 201710017862.9 dated Jan. 3, 2019.
Office Action issued in corresponding Japanese Application No. 2017002111 dated Jan. 8, 2019.
U.S. Office Action issued in U.S. Appl. No. 15/389,785 dated Mar. 8, 2019.

\* cited by examiner

METHOD FOR PREPARING POLYARYLENE SULFIDE (PAS) MONOMER

CROSS REFERENCE TO RELATED APPLICATIONS

This non-provisional application claims the benefit under 35 U.S.C. § 119(e) to U.S. Provisional Application No. 62/277,091, filed on Jan. 11, 2016, which is hereby expressly incorporated by reference into the present application.

BACKGROUND

1. Technical Field

The technical field relates to a method for preparing polyarylene sulfide (PAS) monomer.

2. Description of the Background Art

Polyarylene sulfide (PAS), specifically polyphenylene sulfide (PPS), is a material with good mechanical properties and excellent thermal and chemical resistance compared to metals of the electronic and automobile industry. PAS is also useful in spinning fibers of filters, connectors, coating material, and electronic components. Conventionally, the preparation of PAS was formed by reacting p-dichlorobenzene and sodium sulfide as monomers. A massive byproduct of alkali metal halide resided in the PAS resin, so the PAS resin needed some purification steps. However, the purification by removal of the byproduct increases the production cost, degrades the quality, and decreases the efficiency of the production of PAS resin.

JP 07-304872 A discloses that the monomeric cationic intermediate of polyphenylene sulfide (PPS), including a sulfonium group, was prepared by combining thioanisole and methylphenyl sulfoxide by an electrophilic substitution mechanism in an acidic condition, and this intermediate was demethylated to obtain a neutral dithioether compound as shown by (1) in the reaction scheme below. Subsequently, $Br_2$ and $KHCO_3$ were introduced to oxidate the neutral dithioether compound to obtain a PPS monomer with a sulfoxide group after purification as shown by (1) in the reaction scheme below. Then, the PPS monomer is reacted in an acid to obtain a polysulfonium intermediate, and the polysulfonium intermediate is demethylated to obtain a neutral PAS resin as shown by (2) in the reaction scheme below.

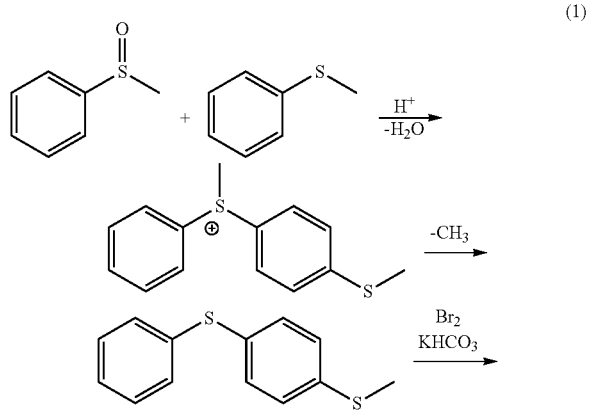

(1)

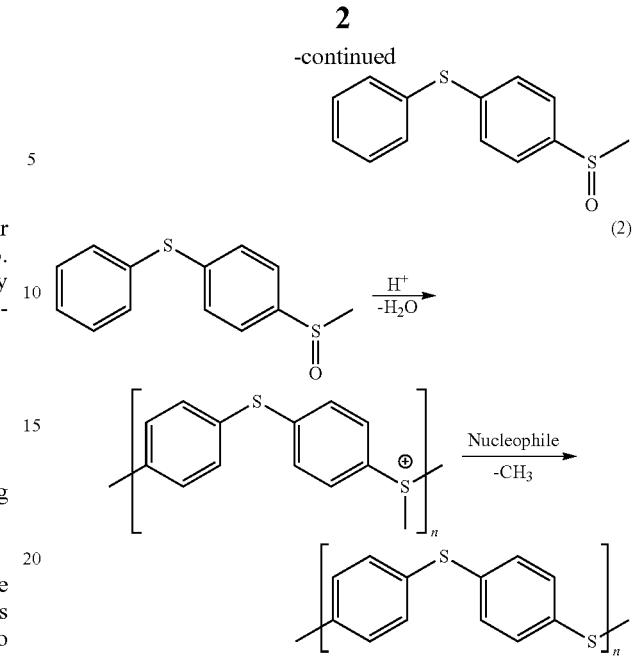

(2)

However, the use of a halogen such as $Br_2$ for oxidation is disadvantageous. Specifically, the halogen results in increased cost due to the additional steps needed to purify the PAS resin. In addition, the halogen is not environmentally friendly. Therefore, an industry-wide need exists for a method of preparing a polyarylene sulfide monomer without a halogen.

SUMMARY

The disclosed embodiments relate to methods of preparing a PAS monomer without a halogen. More specifically, in the disclosed embodiments, a selective oxidation process in producing the PAS monomer prevents the formation of byproducts of sulfones and sulfoxides due to different oxidation states.

The first embodiment is directed to a method for preparing a cationic sulfoxide intermediate having the following formula (1):

(1)

wherein $Ar_1$ and $Ar_2$ are substituted or unsubstituted aryl group that are the same or different, comprising reacting hydrogen peroxide with (i) a compound having the following formula (2) or sulfonic acid $R'SO_3H$ (wherein R' is $CH_3$, $CF_3$, phenyl, toluene, or OH) and (ii) a cationic thioether intermediate having the following formula (4) to obtain the cationic sulfoxide intermediate:

(2)

wherein R is a substituted or unsubstituted $C_1$-$C_6$ alkyl group; and

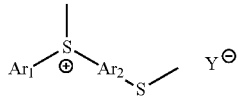
(4)

wherein $Ar_1$ and $Ar_2$ are as defined above and Y is an anion.

The second embodiment is directed to a method for preparing a polyarylene sulfide monomer having the following formula (7):

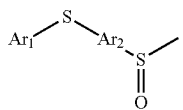
(7)

wherein $Ar_1$ and $Ar_2$ are substituted or unsubstituted aryl groups that are the same or different. The method comprises the method for preparing a cationic sulfoxide intermediate as discussed above and as represented by formula (1) and demethylating the cationic sulfoxide intermediate to obtain the polyarylene sulfide monomer of formula (7).

The third embodiment is directed to a method for preparing a polyarylene sulfide having the following formula (8):

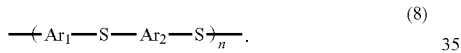
(8)

The method comprises polymerizing a polyarylene sulfide monomer as discussed above and as represented by formula (7). $Ar_1$ and $Ar_2$ are substituted or unsubstituted aryl groups that may be the same or different, and n is 1 to 1000.

Further scope of applicability of the disclosed embodiments will become apparent from the detailed description given hereinafter. However, it should be understood that the detailed description and specific examples, while indicating alternative embodiments of the disclosed embodiments, are given by way of illustration only, since various changes and modifications within the spirit and scope of the disclosed embodiments will become apparent to one of ordinary skill in the art from this detailed description.

BRIEF DESCRIPTION OF THE DRAWINGS

The disclosed embodiments will become more fully understood from the detailed description given below and the accompanying drawings that are given by way of illustration only and are thus not limitative of the disclosed embodiments.

DETAILED DESCRIPTION OF THE DISCLOSED EMBODIMENTS

Figure 1:
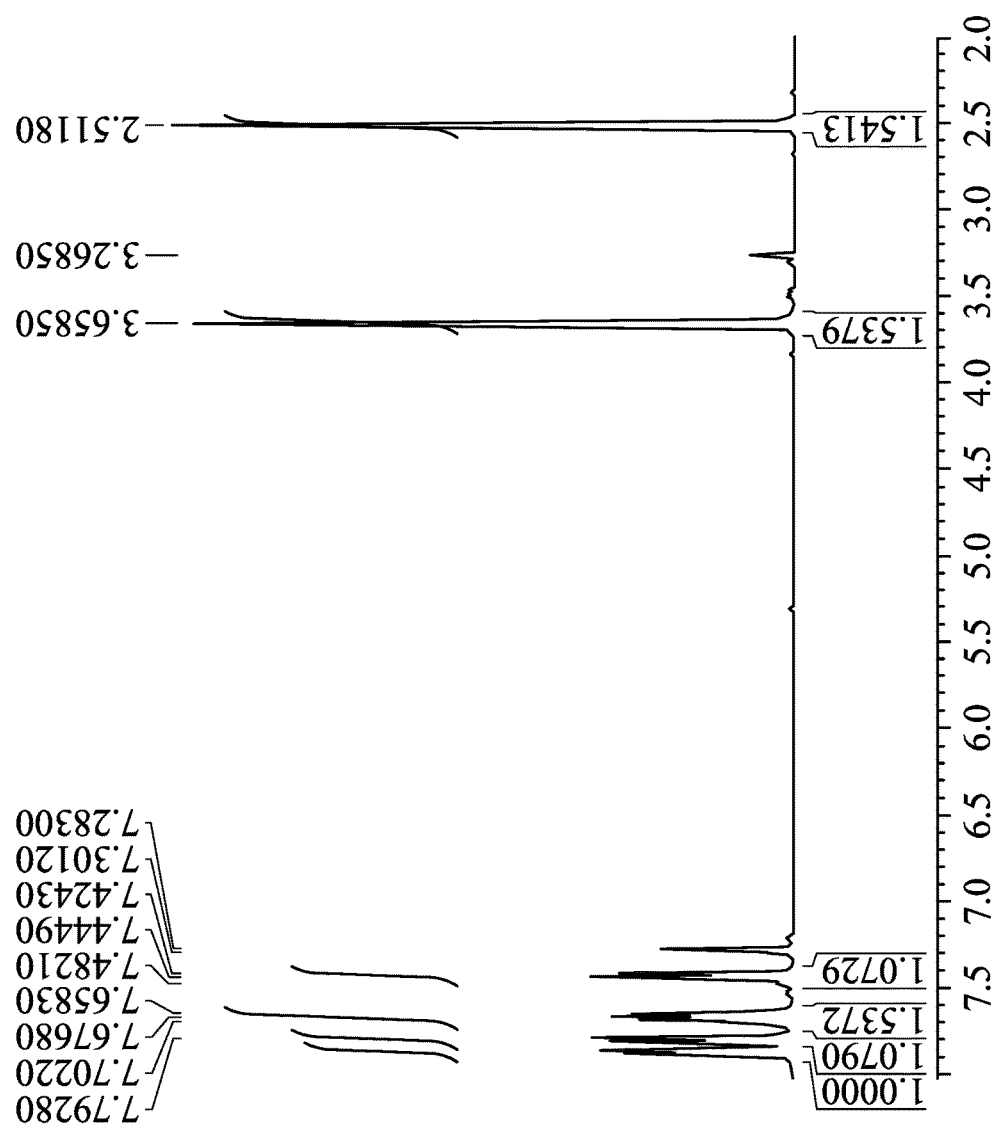
FIG. 1 is a nuclear magnetic resonance (NMR) spectrum of the methylphenyl[4-(methylthio)phenyl]sulfonium perchlorate produced in the examples.

In the following detailed description, for purposes of explanation, numerous specific details are set forth in order to provide a thorough understanding of the disclosed embodiments.

It will be apparent, however, that one or more embodiments may be practiced without these specific details. The inventive concept may be embodied in various forms without being limited to the exemplary embodiments set forth herein.

A first embodiment is directed to a method for preparing a cationic sulfoxide intermediate having the following formula (1):

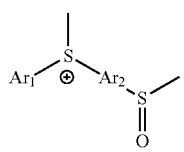
(1)

wherein $Ar_1$ and $Ar_2$ are substituted or unsubstituted aryl groups that are the same or different and may be a phenyl group, a biphenyl group, a naphthyl group, a thienyl group, a tolyl group, a xylyl group, an indolyl group, a tetrahydronaphthyl group, a phenanthrenyl group, a biphenylenyl group, an indenyl group, an anthracenyl group, or a fluorenyl group. The aryl group may have a single ring, two fused rings, or three fused rings. In one embodiment, the aryl group may be a phenyl or biphenyl group.

The method for preparing the cationic sulfoxide intermediate comprises reacting hydrogen peroxide with (i) a compound having the following formula (2) or sulfonic acid

(wherein R' is $CH_3$, $CF_3$, phenyl, toluene, or OH) and (ii) a cationic thioether intermediate having the following formula (4) to obtain the cationic sulfoxide intermediate:

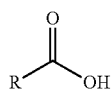
(2)

wherein R is a substituted or unsubstituted $C_1$-$C_6$ alkyl group; and

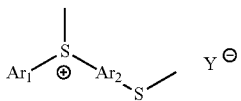

wherein $Ar_1$ and $Ar_2$ are as defined above and Y is an anion. In one embodiment, Y is represented by such as $HSO_4$, $CH_3SO_3$, $PhSO_3$, $p\text{-}tolSO_3$ or $CF_3SO_3$.

In one embodiment, the method for preparing the cationic sulfoxide intermediate may comprise reacting hydrogen peroxide with the compound having the formula (2) to obtain a compound having the following formula (3A):

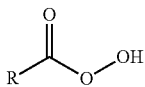

wherein R is a substituted or unsubstituted $C_1$-$C_6$ alkyl group; and reacting the compound having the formula (3A) with the cationic thioether intermediate (4).

In one embodiment, the method for preparing the cationic sulfoxide intermediate may comprise reacting hydrogen peroxide with sulfonic acid $R'SO_3H$ to obtain a compound having the following formula (3B):

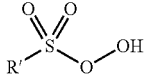

wherein R' is $CH_3$, $CF_3$, phenyl, toluene, or OH; and reacting the compound having the formula (3B) with the cationic thioether intermediate (4).

In one embodiment, the molar ratio of hydrogen peroxide to the compound having the formula (2) may be 2:1 to 4:1. Similarly, the molar ratio of hydrogen peroxide to sulfonic acid $R'SO_3H$ may be 2:1 to 4:1.

In one embodiment, R may be a methyl group. R may be linear or a cyclic alkyl group from C1 to C6.

In one embodiment, the cationic thioether intermediate (4) may be first mixed with the compound having the formula (2), and then, hydrogen peroxide may be added.

In one embodiment, the reaction may proceed at about 20° C. to 25° C. for 80 minutes to 90 minutes.

The cationic thioether intermediate may be prepared by a method of reacting the compound having the formula (5):

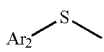

and the compound having the following formula (6):

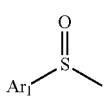

in acidic conditions wherein $Ar_1$ and $Ar_2$ is defined the same as $Ar_1$ and $Ar_2$ above. $Ar_1$ and $Ar_2$ may be phenyl or biphenyl groups. As such, the compound of formula (5) may be thioanisole or methyl biphenyl sulfide. The compound of formula (6) may be methyl phenyl sulfoxide. In one embodiment, the acidic conditions may be produced by adding sulfonic acid $R'SO_3H$ wherein R' is $CH_3$, $CF_3$, phenyl, toluene, or OH. In other words, the acidic conditions may be produced by adding methanesulfonic acid, benzenesulfonic acid, p-toluenesulfonic acid, sulfuric acid, or trifluoromethane sulfonic acid. In one embodiment, the same parts by mole of thioanisole and methyl phenyl sulfoxide are mixed and reacted in acidic condition from 0 to 25° C. in 1 atm. In one embodiment, the compounds of formula (5) and formula (6) may be combined at about 0° C., and the temperature may be raised to room temperature (i.e., about 18° C. to 25° C.) after an acid is added. In one embodiment, the reaction may continue for about 10 hours to 30 hours (i.e., about 20 hours).

The first embodiment, using a compound having the formula (2), is represented in the following reaction scheme:

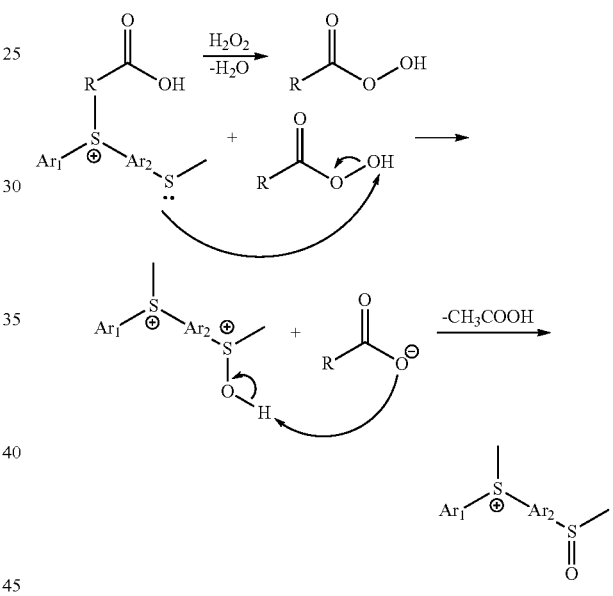

The first embodiment, using a sulfonic acid $R'SO_3H$, is represented in the following reaction scheme:

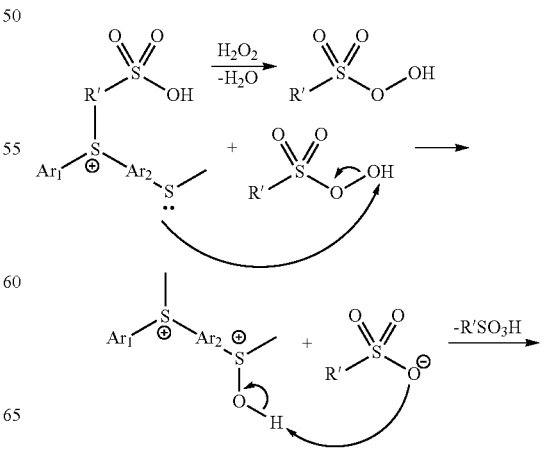

-continued

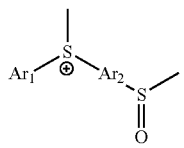

A second embodiment is directed to a method for preparing a polyarylene sulfide monomer having the following formula (7):

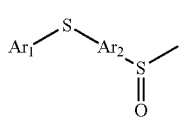

(7)

wherein $Ar_1$ and $Ar_2$ are aryl groups that may be the same or different and may be a phenyl group, a biphenyl group, a naphthyl group, a thienyl group, a tolyl group, a xylyl group, an indolyl group, a tetrahydronaphthyl group, a phenanthrenyl group, a biphenylenyl group, an indenyl group, an anthracenyl group, or a fluorenyl group. The aryl group may have a single ring, two fused rings, or three fused rings. The aryl group may be a phenyl or biphenyl group. The polyarylene sulfide monomer may be methyl 4-(phenylthio) phenyl sulfoxide. This method may not use a halogen.

The first step for preparing the polyarylene sulfide monomer comprises the method for preparing a cationic sulfoxide intermediate as discussed above.

In the next step, the cationic sulfoxide intermediate is demethylated to obtain the polyarylene sulfide monomer of formula (7).

The efficient nucleophiles are chosen for demethylation of the cationic thioether intermediate (4), and the nucleophiles may be substituted or unsubstituted amine, amide, pyridine, or halide compounds from about 20° C. to 150° C. in 1 atm. In one embodiment, the reaction may proceed for about 20 minutes to 6 hours.

The second embodiment is represented in the following reaction scheme:

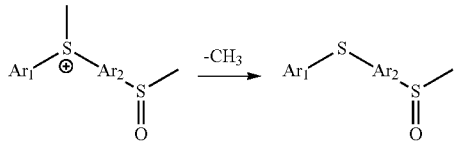

A third embodiment is directed to a method for preparing a polyarylene sulfide having the following structure according to formula (8):

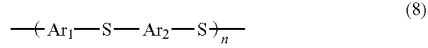

(8)

wherein $Ar_1$ and $Ar_2$ are aryl groups that may be the same or different and may be a phenyl group, a biphenyl group, a naphthyl group, a thienyl group, a tolyl group, a xylyl group, an indolyl group, a tetrahydronaphthyl group, a phenanthrenyl group, a biphenylenyl group, an indenyl group, an anthracenyl group, or a fluorenyl group. The aryl group may have a single ring, two fused rings, or three fused rings. In one embodiment, the aryl group may be a phenyl group. As such, the polyarylene sulfide may be polyphenylene sulfide.

n is an integer ranging from 1 to 1000 or from 2 to 1000.

The PAS is prepared by polymerizing the polyarylene sulfide monomer prepared by the method discussed above.

In one embodiment, the same parts by mole of thioanisole and methyl phenyl sulfoxide may be mixed and reacted in acidic condition from about 0° C. to 25° C. in about 1 atm, and the used acid may be sulfonic acid $R'SO_3H$ wherein $R'$ is $CH_3$, $CF_3$, phenyl, toluene, or OH. In other words, the used acid may be methanesulfonic acid, benzenesulfonic acid, p-toluenesulfonic acid, sulfuric acid, or trifluoromethane sulfonic acid. In the next step, the cationic sulfoxide intermediate may be demethylated to obtain the polyarylene sulfide monomer of formula (7). The efficient nucleophiles are chosen for demethylation of the cationic thioether intermediate (4), and the nucleophiles may be substituted or unsubstituted amine, amide, pyridine, or halide compounds from 20 to 150° C. in 1 atm. In one embodiment, the reaction proceeds for 20 minutes to 6 hours.

In one embodiment, the polyarylene sulfide monomer is reacted with an acid to obtain a pulysulfonium intermediate having the following structure according to formula (9):

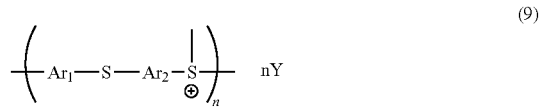

(9)

wherein $Ar_1$ and $Ar_2$ are aryl groups that may be the same or different and may be a phenyl group, a biphenyl group, a naphthyl group, a thienyl group, a tolyl group, a xylyl group, an indolyl group, a tetrahydronaphthyl group, a phenanthrenyl group, a biphenylenyl group, an indenyl group, an anthracenyl group, or a fluorenyl group. The aryl group may have a single ring, two fused rings, or three fused rings. In one embodiment, the aryl group may be a phenyl group.

n is an integer ranging from 1 to 1000 or from 2 to 1000.

Y is represented by anions, such as $HSO_4^-$, $CH_3SO_3^-$, $PhSO_3^-$, p-tol$SO_3^-$ or $CF_3SO_3^-$.

The acid may be sulfonic acid $R'SO_3H$ wherein $R'$ is $CH_3$, $CF_3$, phenyl, toluene, or OH. In other words, the acid may be sulfuric acid, methanesulfonic acid, benzenesulfonic acid, p-toluenesulfonic acid, or trifluoromethanesulfonic acid.

In one embodiment, the polyarylene sulfide monomer and the acid may be reacted at about 0° C. for about 30 minutes to 1 hour, and then, the temperature of the reaction may be raised to room temperature (i.e., about 18° C. to 25° C.) for about 10 hours to 30 hours (i.e., about 20 hours).

In the next step, the polysulfonium intermediate (9) is demethylated to obtain the polyarylene sulfide (8). The polysulfonium intermediate may be demethylated with a nucleophile. The nucleophile may be aqueous HCl, HBr, HI, amines, amides or pyridines. In this regard, the acidity of the acid used for demethylation may be stronger than the acid used to obtain the polysulfonium intermediate. The polysulfonium intermediate may be demethylated in an organic solvent. The organic solvent may be at least one selected from the group consisting of water, ketones, nitriles, sulfones and amides. In one embodiment, the organic solvent may be a mixed solvent with water. In another embodiment, the organic solvent may be a mixed solvent of water and acetone. The efficient nucleophiles are chosen for demethylation of the polysulfonium intermediate, and the nucleophiles may be substituted or unsubstituted amine, amide, pyridine, or halide compounds from about 20° C. to 150° C. in about 1 atm. In one embodiment, the reaction proceeds for about 4 hours to 72 hours. In another embodiment, the reaction may proceed for about 20 hours to 24 hours at a temperature of room temperature up to 100° C. Room temperature is defined as being about 18° C. to 25° C.

The third embodiment is represented in the following reaction scheme:

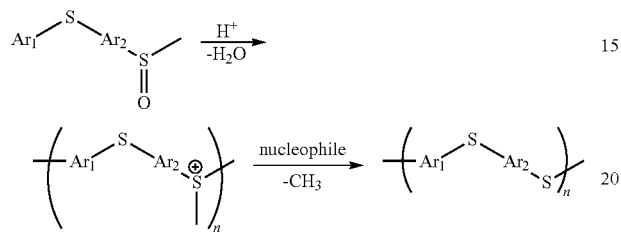

One example of a reaction scheme of the disclosed embodiment is shown below wherein a cationic intermediate with a sulfonium group is obtained by reacting thioanisole and methylphenyl sulfoxide in an acidic condition. Subsequently, a moderate oxidant is selected to oxidize the thioether group rather than the sulfonium group as shown in Scheme (3). Then, the PPS monomer is obtained after demethylation. Next, polymerization of the PPS monomer occurs as shown in Scheme (4).

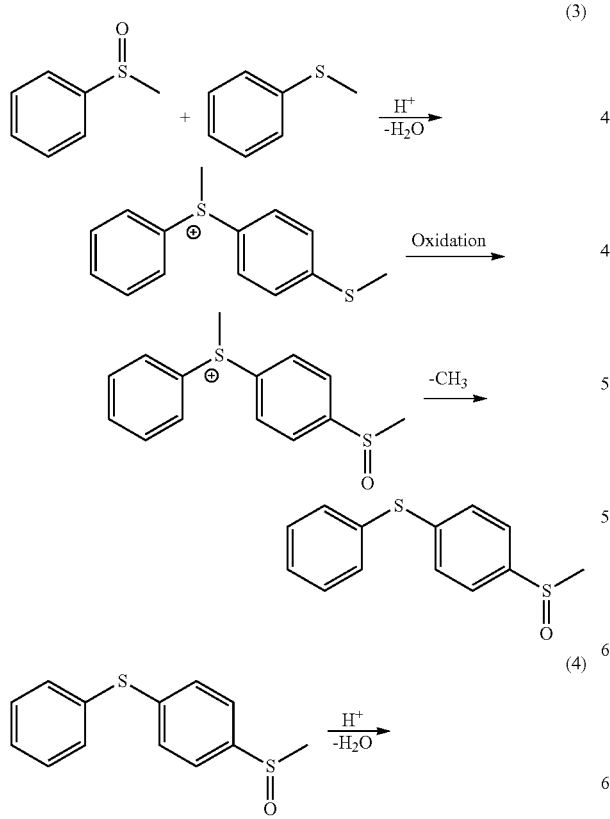

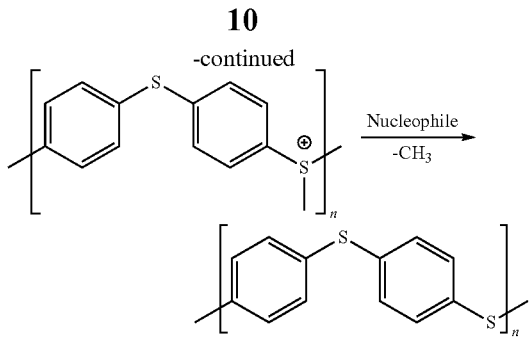

One example of the oxidation step of the disclosed embodiment is shown below wherein the cationic thioether intermediate is oxidized with acetic peroxide to obtain a cationic sulfoxide intermediate. The acetic peroxide may be obtained by mixing hydrogen peroxide and acetic acid.

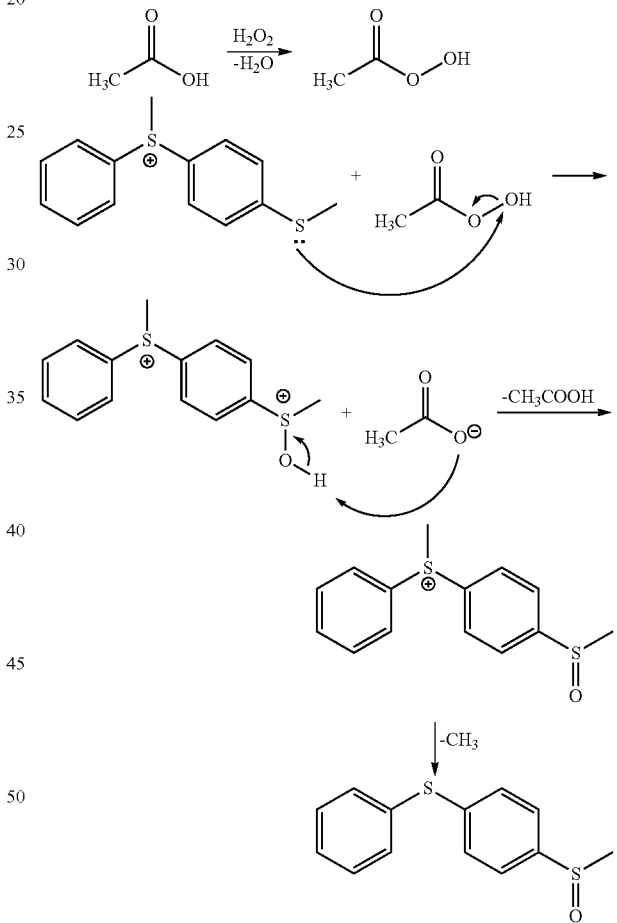

The acetic peroxide may be prepared by mixing hydrogen peroxide and acetic acid. The acetic peroxide may then be used to oxidize the cationic thioether intermediate. The methyl group and positive charge on the sulfonic group provides a steric and electric hindrance for selective oxidation on the thioether group. In other words, the sulfonium group has a positive charge and a steric blocked group (i.e., an alkyl group) that prevents the sulfonium group from being oxidized when one or more than one oxidant exists. A moderate oxidant may be selected to oxidize the thioether group without oxidizing the sulfonium group to obtain an intermediate of a PAS monomer. Subsequently, the PAS monomer can be prepared after demethylating the sulfonium group.

In contrast, conventional methods do not use selective oxidation because a different oxidant, specifically a halogen, is used. However, this type of oxidation may oxidize the sulfonium group. To avoid these problems of conventional methods, the disclosed embodiment does not use a halogen.

In addition, unlike conventional methods, the disclosed embodiment may conduct the oxidation step prior to the demethylation step. In contrast, conventional methods perform the demethylation step followed by the oxidation step.

The disclosed embodiment will hereinafter be described with reference to exemplary embodiments, which are written to be understood only as examples and are not intended to limit the scope of the present application.

EXAMPLES

Preparation of methylphenyl[4-(methylthio)phenyl] sulfonium perchlorate

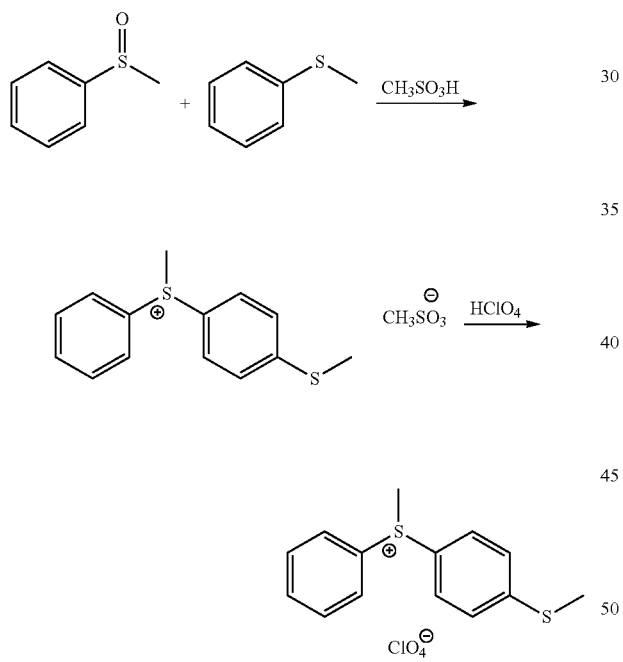

2.9 ml thioanisole and 3.5 g methylphenyl sulfoxide were mixed in a double-necked round-bottom flask with a stirrer and cooled to 0° C. Subsequently, 50 ml methanesulfonic acid was added dropwise, and then the temperature was raised to room temperature. The reaction continued for 20 hr, and the raw product was poured into 100 ml 70% $HClO_4$ and stirred for another 1 hr. Extraction was operated with water and dichloromethane, and the product, thioether sulfonium intermediate, was obtained (yield: 90%). The NMR spectrum of FIG. 1 showed the following values: $^1$H NMR (400 MHz, ppm, $CDCl_3$): 2.5 (—$CH_3$, s), 3.7 (S—$CH_3$, s), 7.4 (phenyl, 2H, d), 7.6 (phenyl, 3H, t), 7.7-7.8 (phenyl, 4H, m).

Preparation of PPS monomer with methylphenyl[4-(methylthio)phenyl] sulfonium perchlorate

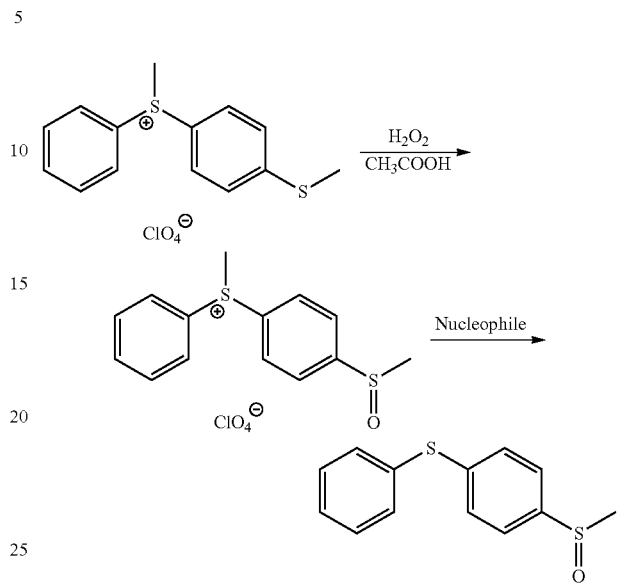

Figure 2:
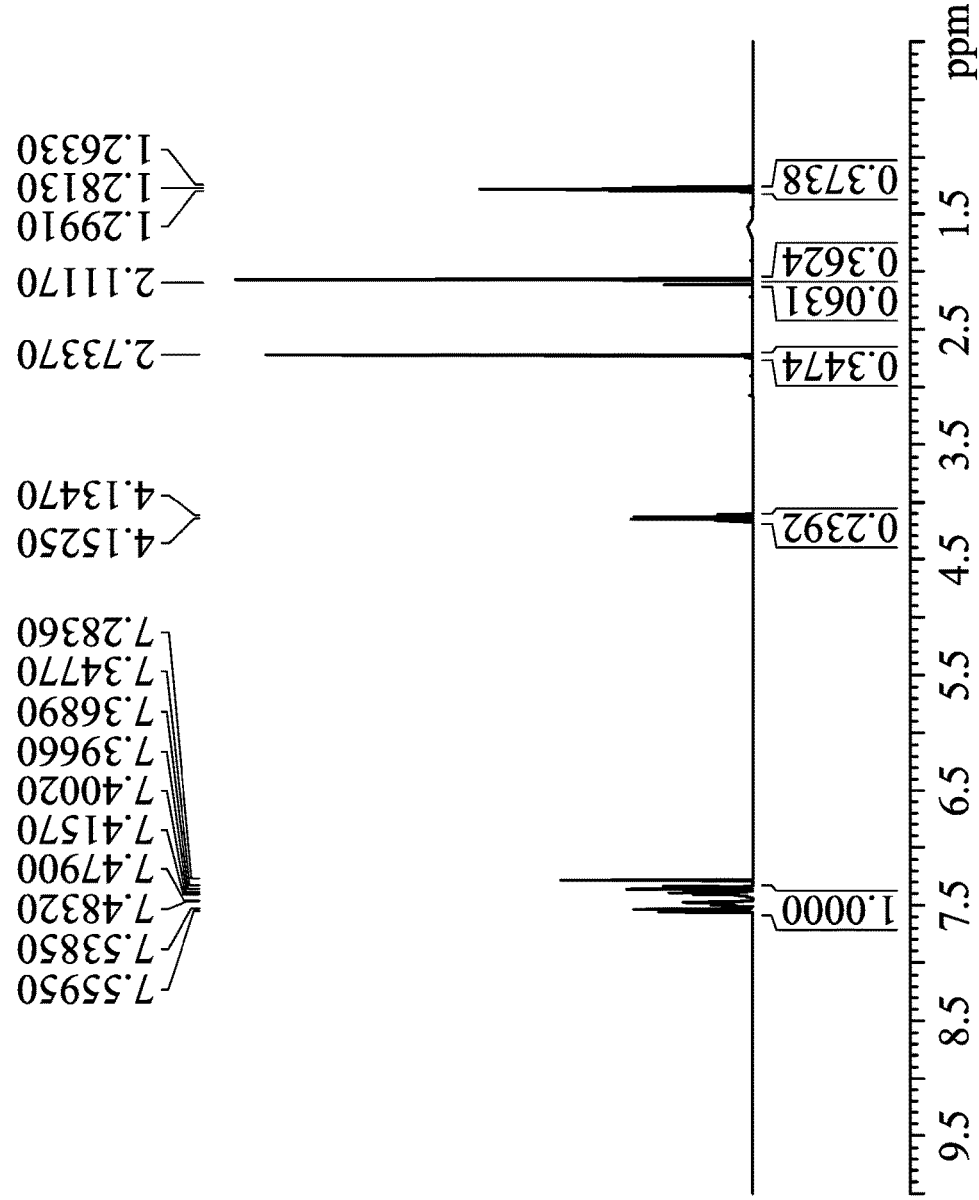
FIG. 2 is a nuclear magnetic resonance (NMR) spectrum of the methyl 4-(phenylthio)phenyl sulfoxide produced in the examples.

1 g methylphenyl[4-(methylthio)phenyl] sulfonium perchlorate and 3 ml glacial acetic acid were mixed in a double-necked round-bottom flask with a stirrer. The mixture was stirred in a water bath at 20° C., and 0.9 ml 30% hydrogen peroxide was introduced dropwise. Subsequently, the reaction proceeded continuously for 80 min. After the reaction was finished, organic solvent was utilized to extract the cationic sulfoxide intermediate with water. 0.97 g of intermediate was obtained. The cationic sulfoxide intermediate was dissolved in 10 ml acetonitrile, and 30 ml 10% KCl was introduced dropwise. The mixture was refluxed for 6 hr, and extraction was operated by water and dichloromethane triply. 0.63 g PPS monomer was obtained (yield: 88%). The NMR spectrum of FIG. 2 showed the following values: $^1$H NMR (400 MHz, ppm, $CDCl_3$): 2.73 (—$CH_3$, s), 7.35-7.56 (phenyl, 9H, m).

Preparation of methyl phenyl [4-(methylthio)biphenyl]sulfonium perchlorate

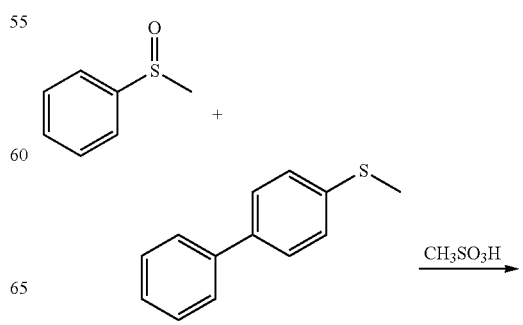

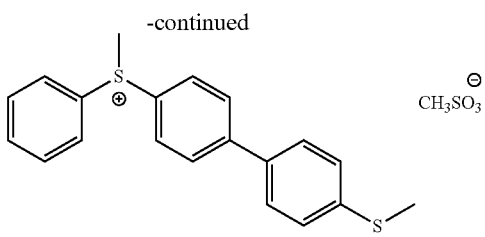

Figure 3:
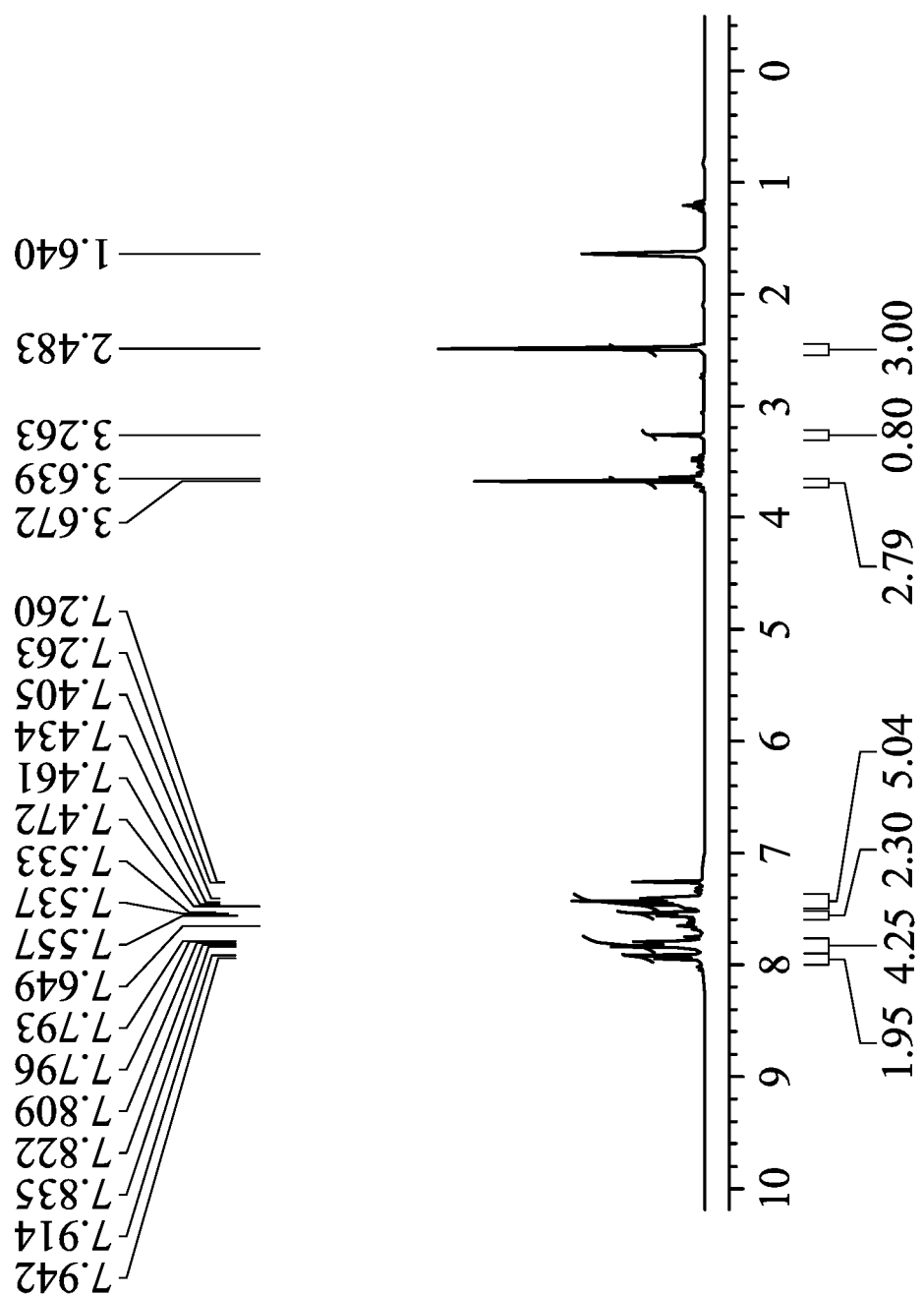
FIG. 3 is a nuclear magnetic resonance (NMR) spectrum of the methyl phenyl [4-(methylthio)biphenyl]sulfonium perchlorate produced in the examples.
Figure 4:
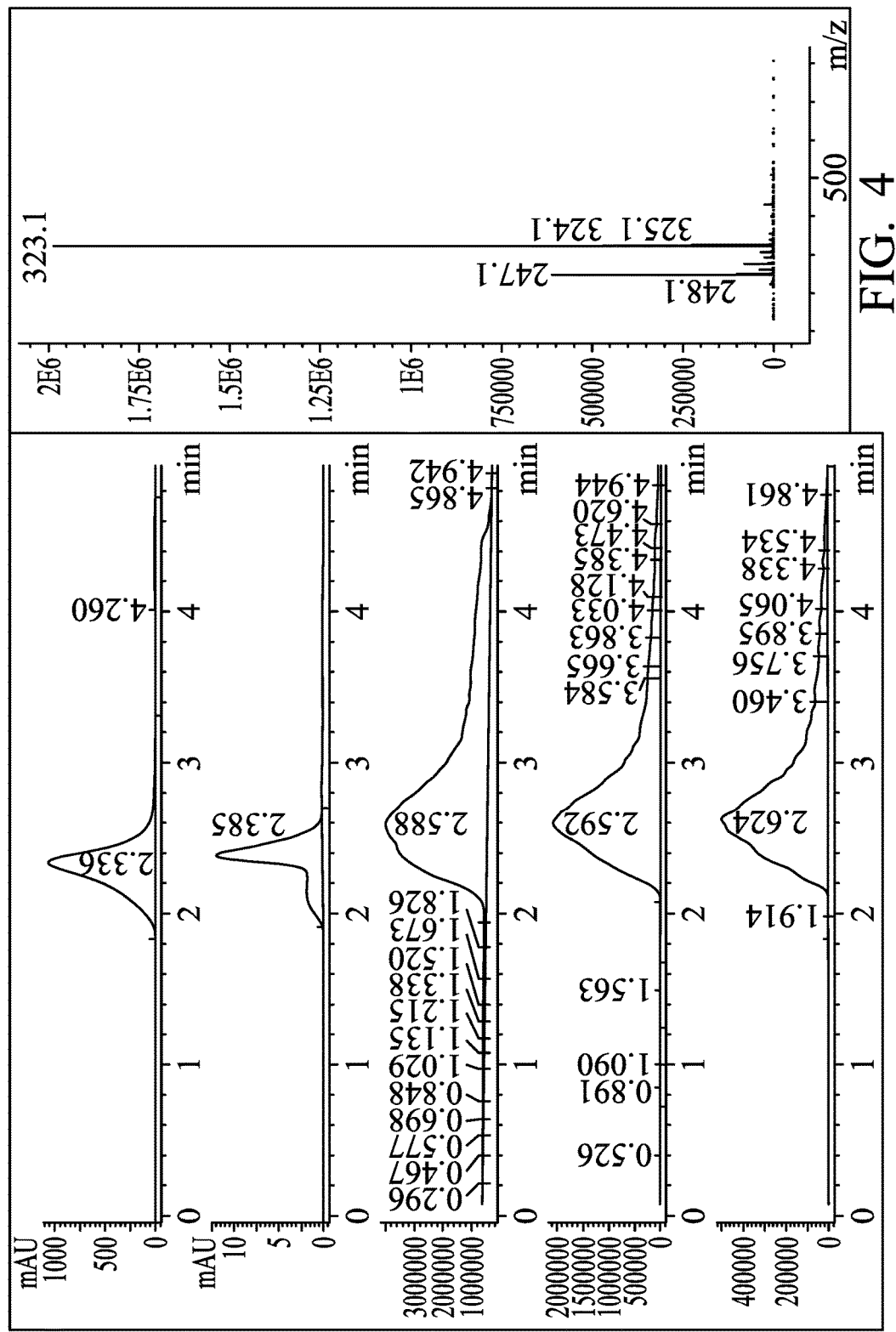
FIG. 4 is a liquid chromatography-mass spectrometry (LC-MS) spectrum of the methyl phenyl [4-(methylthio) biphenyl]sulfonium perchlorate produced in the examples.

1 g methyl biphenyl sulfide and 0.7 g methylphenyl sulfoxide were mixed in a double-necked round-bottom flask with a stirrer and cooled to 0° C. Subsequently, 10 ml methanesulfonic acid was added dropwise, and then, the temperature was raised to room temperature. The reaction continued for 20 hr, and a brown raw product was poured into 40 ml 70% $HClO_4$ and stirred for another 1 hr. Extraction was operated with water and dichloromethane, and the product, thioether sulfonium intermediate, was prepared (yield: 92%). The scheme is shown above. FIG. 3 shows the NMR spectrum of the compound, and the m/z of methyl phenyl [4-(methylthio)biphenyl] sulfonium in the LC-MS spectrum was 323 as shown in FIG. 4. $^1$H NMR (400 MHz, ppm, $CDCl_3$): 2.48 (—$CH_3$, s), 3.67 (sulfonium-$CH_3$, s), 7.40-7.94 (aromatic H, 13H, m).

Preparation of PAS monomer with methyl phenyl [4-(methylthio)biphenyl]sulfonium perchlorate

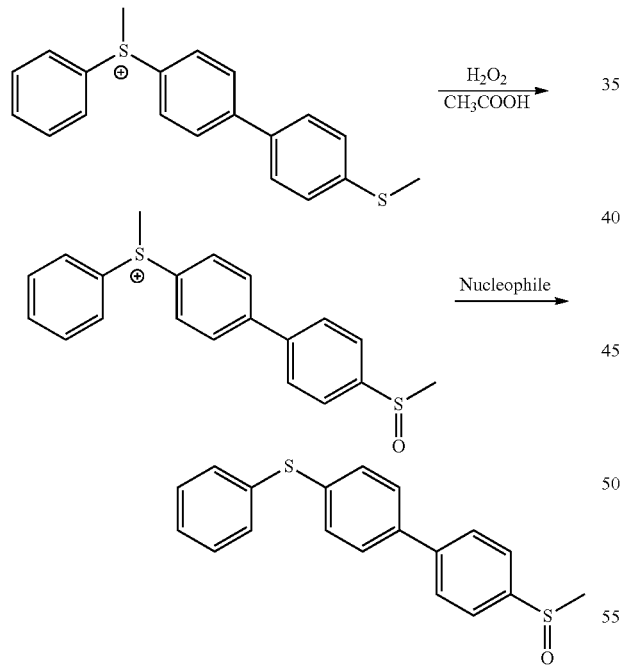

Figure 5:
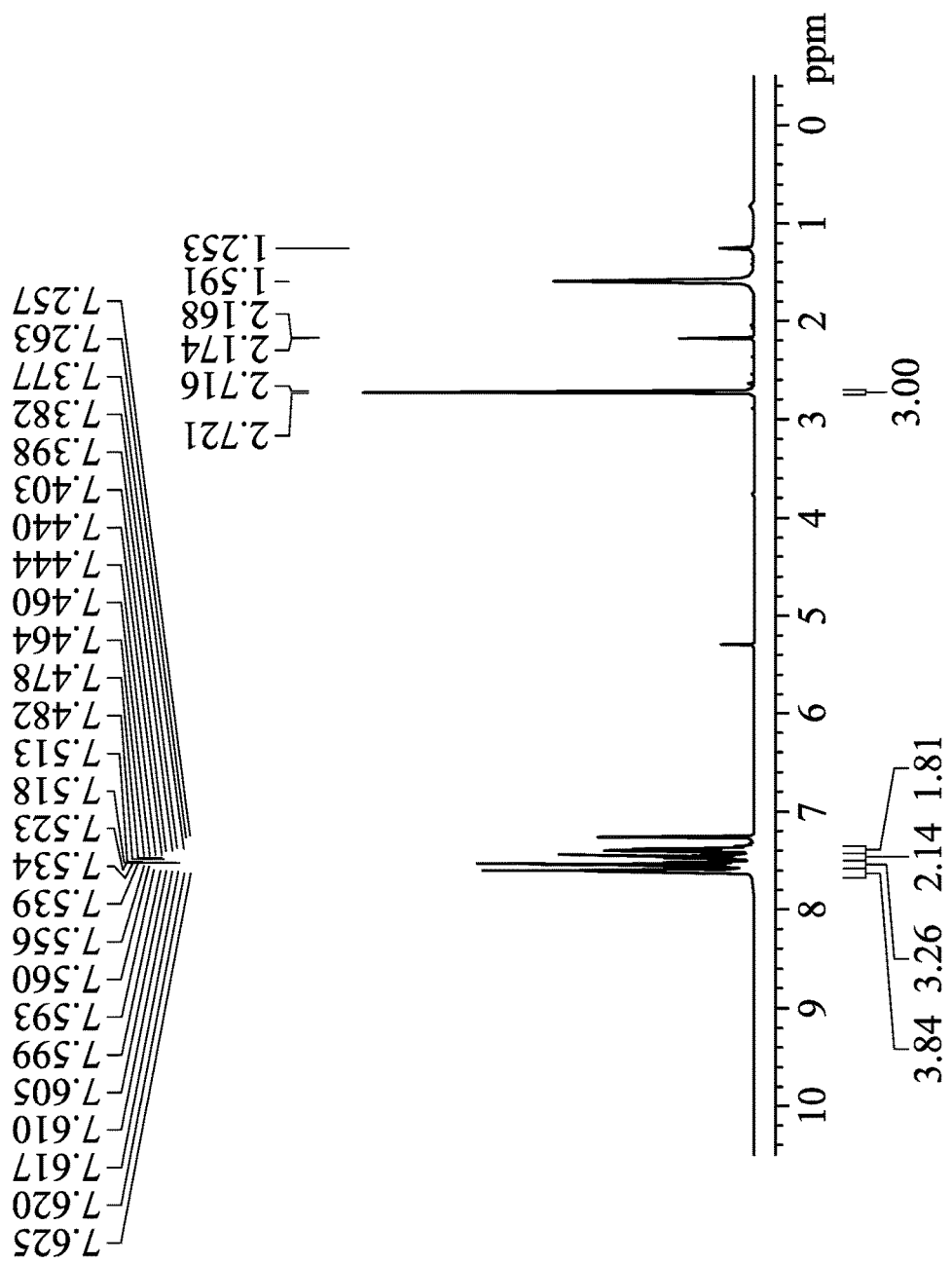
FIG. 5 is a nuclear magnetic resonance (NMR) spectrum of the methyl 4-(phenylthio)biphenyl sulfoxide produced in the examples.
Figure 6:
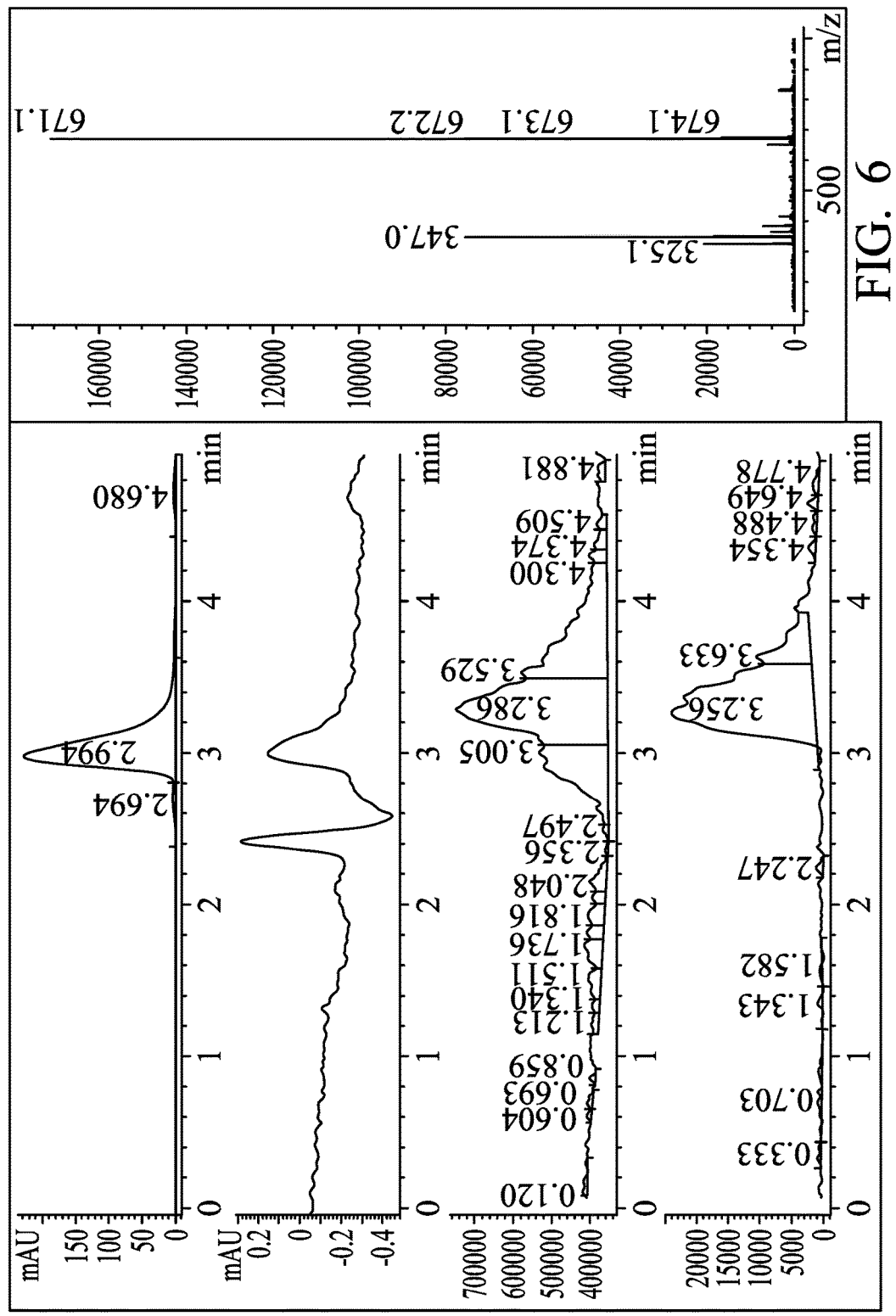
FIG. 6 is a liquid chromatography-mass spectrometry (LC-MS) spectrum of the methyl 4-(phenylthio)biphenyl sulfoxide produced in the examples.

1.9 g methyl phenyl [4-(methylthio)biphenyl] sulfonium perchlorate and 30 ml glacial acetic acid were mixed in a double-necked round-bottom flask with a stirrer. The mixture was stirred in a water bath at 20° C., and 2.02 ml 30% hydrogen peroxide was introduced dropwise. Subsequently, the reaction proceeded continuously for 90 min. After the reaction was finished, organic solvent was utilized to extract the cationic sulfoxide intermediate with water to obtain an orange intermediate. The cationic sulfoxide intermediate was dissolved in 10 ml 4-picoline. The reaction proceeded for 30 min and was refluxed continuously for another 20 min. Extraction was operated subsequently by water and dichloromethane triply to obtain 1 g PPS monomer (yield: 69%). FIG. 5 shows the NMR spectrum of the compound. $^1$H NMR (400 MHz, ppm, $CDCl_3$): 2.72 (—$CH_3$, s), 7.38-7.63 (aromatic H, 13H, m). The m/z signals of methyl 4-phenylthio)biphenyl sulfoxide were 325($M+H^+$), 347($M+Na^+$) and 671($2*M+Na^+$) as shown in FIG. 6.

Preparation of PPS

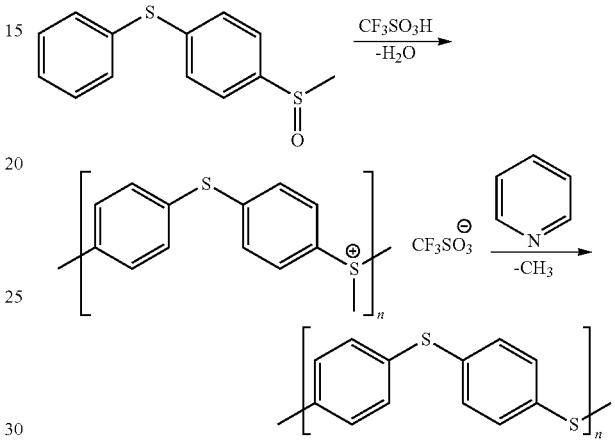

1 g methyl-4-(phenylthio)phenyl sulfoxide was added in a double-necked round-bottom flask with a stirrer and cooled to 0° C. Subsequently, 5 ml trifluoromethanesulfonic acid was added dropwise at 0° C., and then the temperature was raised to room temperature slowly during a period of 0.5-1 hour. The reaction continued for 20 hours, and the raw product was washed with 100 ml ice water several times and dried in vacuum. A white precipitate (1.4 g, yield: 95%) of a polycationic intermediate was obtained.

Figure 7:
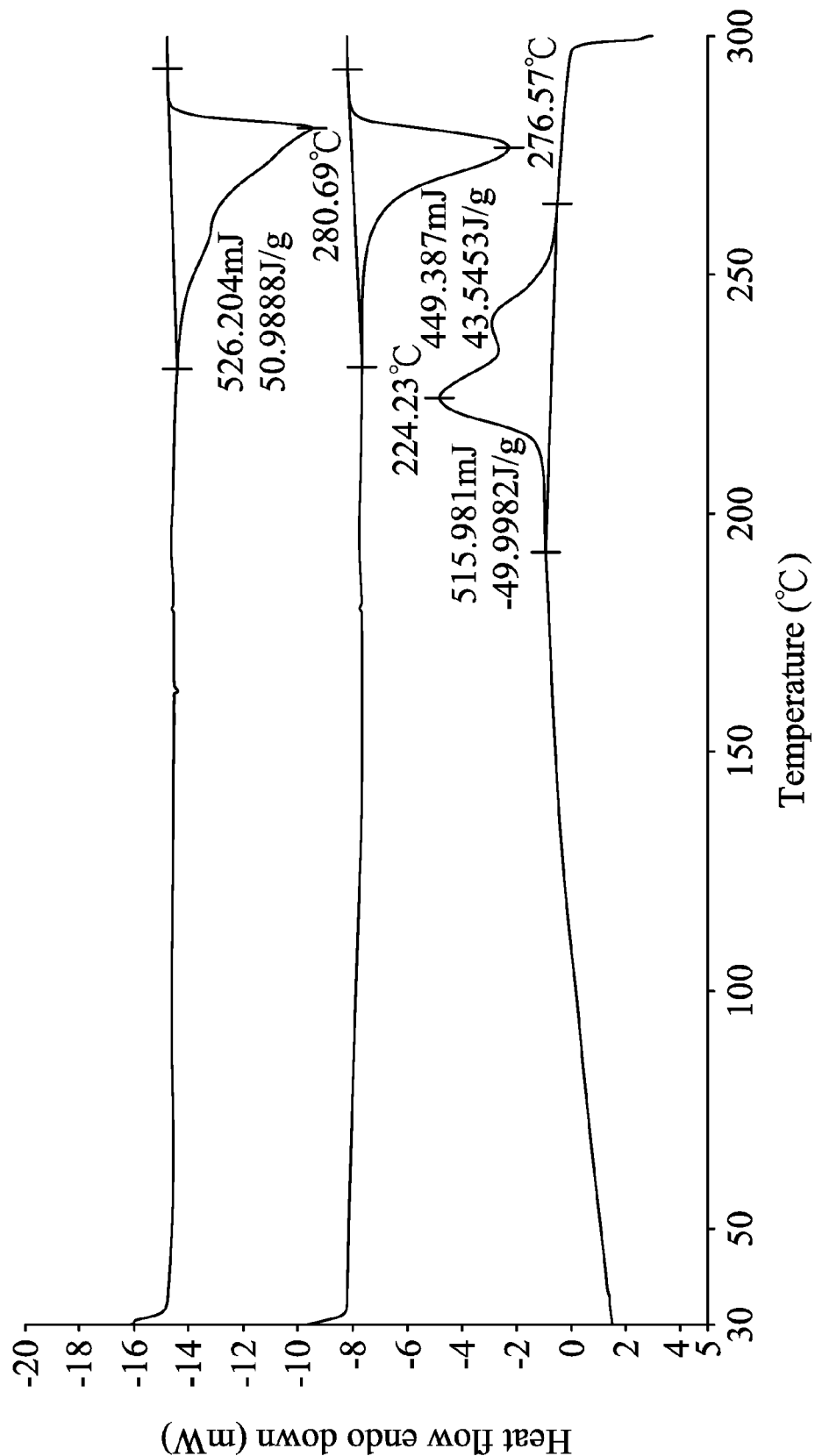
FIG. 7 is a differential scanning calorimetry (DSC) spectrum of the polyphenylene sulfide produced in the examples.

0.95 g of the polycationic intermediate was added to a double-necked round-bottom flask with a stirrer. 10 ml 4-picoline was added dropwise, and the reaction continued for 1 hour. The temperature was raised to 100° C., and the reaction processed for about 20 hours. A white powder of PPS was obtained (0.37 g, 70%), and the excess 4-picoline solution was quenched with 200 ml 10% methanol solution. According to the DSC spectrum of FIG. 7, the melting point of the PPS was 280° C.

Preparation of PPS monomer, methyl 4-(phenylthio)phenyl sulfoxide

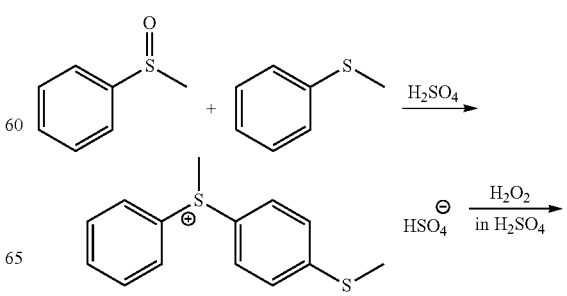

-continued

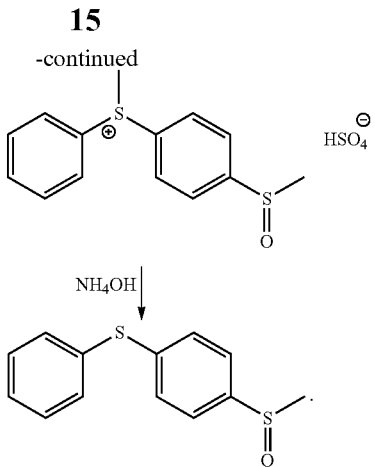

Figure 8:
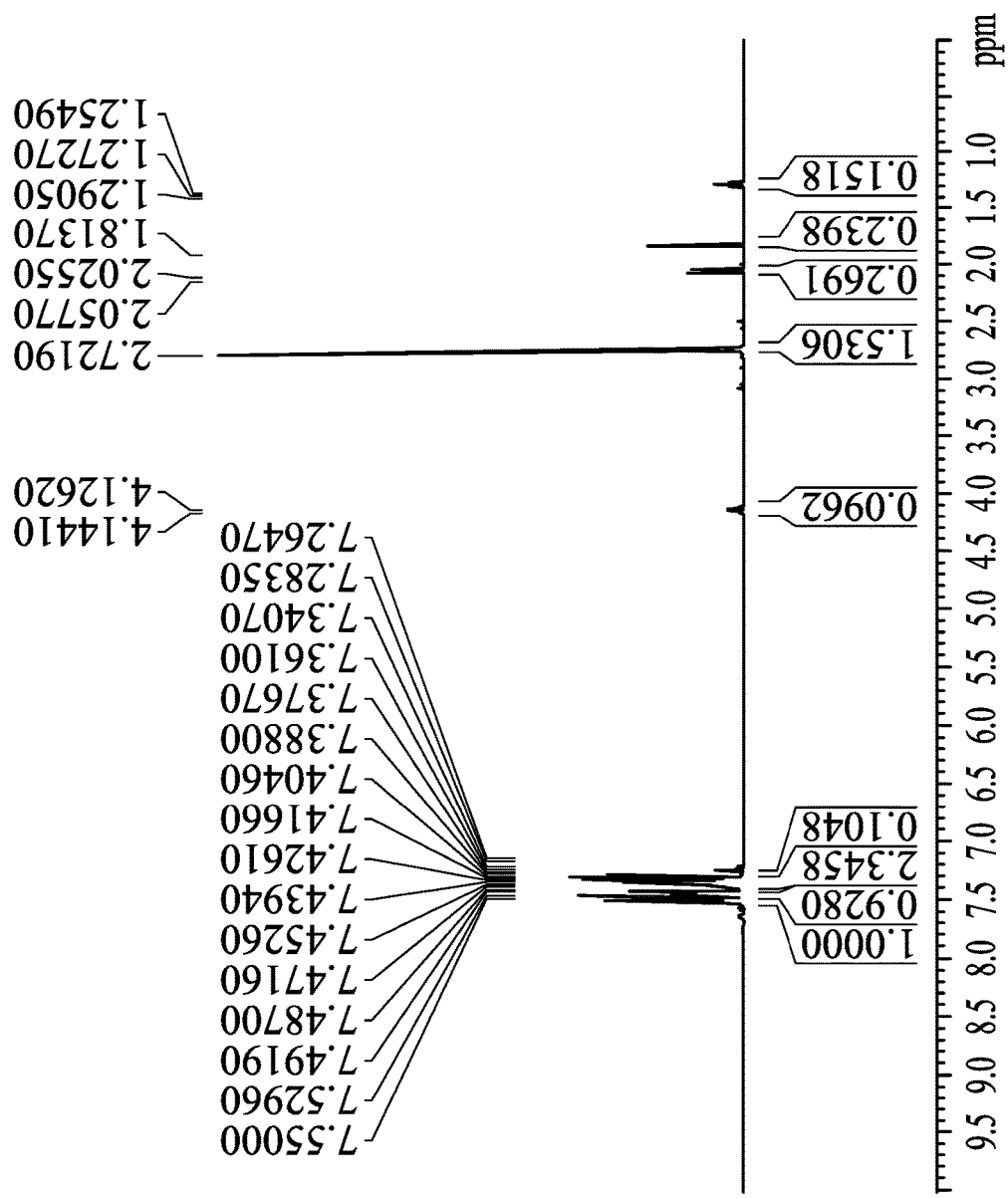
FIG. 8 is a nuclear magnetic resonance (NMR) spectrum of the methyl 4-(phenylthio)phenyl sulfoxide produced in the examples.

2.66 g thioanisole and 3 g methylphenyl sulfoxide were mixed in a double-necked round-bottom flask with a stirrer and cooled to 0° C. Subsequently, 3 ml 97% sulfuric acid was added dropwise, and then the temperature was raised to room temperature. The reaction continued for 20 hours, and then 30 ml water and 2.44 g 30% hydrogen peroxide was induced for another 4 hours at room temperature. Subsequently, 45 ml 30% ammonia was induced for 4 hours at room temperature. Extraction was operated with water and ethyl acetate, and methyl 4-(phenylthio)phenyl sulfoxide was obtained (yield: 90.6%). The NMR spectrum of FIG. 8 showed the following values: $^1$H NMR (400 MHz, ppm, CDCl$_3$): 2.72 (—CH$_3$, s), 7.34-7.55 (phenyl, 9H, m).

It will be apparent to those skilled in the art that various modifications and variations can be made to the disclosed embodiments. It is intended that the specification and examples be considered as exemplary only with a true scope of the disclosure being indicated by the following claims and their equivalents.

The invention claimed is:
1. A method for preparing a polyarylene sulfide monomer having the following formula (7):

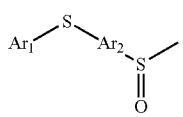

(7)

wherein Ar$_1$ and Ar$_2$ are substituted or unsubstituted aryl groups that are the same or different, comprising:
reacting hydrogen peroxide with (i) R'SO$_3$H, wherein R' is CH$_3$, CF$_3$, phenyl, or toluene, or OH, and (ii) a cationic thioether intermediate having the following formula (4)
to obtain a cationic sulfoxide intermediate having the following formula (1):

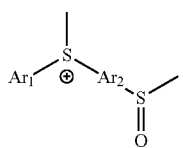

(1)

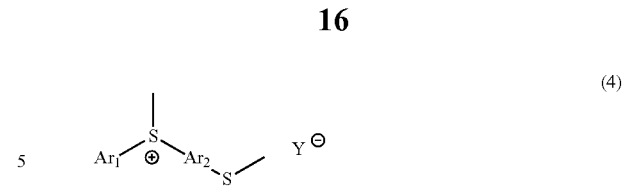

(4)

wherein Ar$_1$ and Ar$_2$ are as defined above and Y is an anion; and
demethylating the cationic sulfoxide intermediate to obtain the polyarylene sulfide monomer.

2. The method of claim 1, wherein the cationic thioether intermediate is prepared by the method comprising:
reacting a compound having the following formula (5):

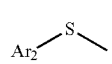

(5)

and a compound having the following formula (6):

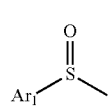

(6)

in acidic conditions wherein Ar$_1$ and Ar$_2$ are substituted or unsubstituted aryl groups that are the same or different.

3. A method for preparing a polyarylene sulfide having the following formula (8):

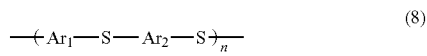

(8)

comprising:
polymerizing a polyarylene sulfide monomer prepared by the method according to claim 1;
wherein Ar$_1$ and Ar$_2$ are substituted or unsubstituted aryl groups that are the same or different and n is 1 to 1000.

4. The method according to claim 1, wherein Ar$_1$ and Ar$_2$ are phenyl groups.

5. The method according to claim 1, wherein R is a methyl group.

6. The method according to claim 1, wherein the method does not use a halogen.

7. The method of claim 2, wherein the compound having the formula (5) is thioanisole or methyl biphenyl sulfide.

8. The method of claim 2, wherein the compound having the formula (6) is methylphenyl sulfoxide.

9. The method of claim 2, wherein the acidic conditions are produced by adding methanesulfonic acid, benzenesulfonic acid, p-toluenesulfonic acid, sulfuric acid, or trifluoromethane sulfonic acid.

10. The method of claim 1, wherein a molar ratio of hydrogen peroxide to R'SO$_3$H is 2:1 to 4:1.

11. The method according to claim 1, wherein said method consists of:
reacting the hydrogen peroxide with (i) R'SO$_3$H, and (ii) the cationic thioether intermediate having formula (4) to obtain the cationic sulfoxide intermediate; and
demethylating the cationic sulfoxide intermediate to obtain the polyarylene sulfide monomer.

12. The method according to claim 1, wherein the hydrogen peroxide is reacted with $R'SO_3H$, wherein R' is $CH_3$, $CF_3$, phenyl, or toluene.

\* \* \* \* \*